(12) United States Patent
Hirakawa et al.

(10) Patent No.: US 11,485,950 B2
(45) Date of Patent: Nov. 1, 2022

(54) CELL STIMULATION DEVICE, CELL CULTURE DEVICE, AND CELL STIMULATION METHOD

(71) Applicant: SHARP KABUSHIKI KAISHA, Sakai (JP)

(72) Inventors: Hiroyuki Hirakawa, Sakai (JP); Haruo Yamamoto, Sakai (JP); Tadashi Iwamatsu, Sakai (JP); Yasuhiro Sakamoto, Sakai (JP); Hiroyuki Yamaji, Sakai (JP); Kohji Shinkawa, Sakai (JP); Mai Takasaki, Sakai (JP); Shohei Komaru, Sakai (JP); Fumiaki Sugimori, Sakai (JP)

(73) Assignee: SHARP KABUSHIKI KAISHA, Osaka (JP)

( * ) Notice: Subject to any disclaimer, the term of this patent is extended or adjusted under 35 U.S.C. 154(b) by 123 days.

(21) Appl. No.: 16/756,080

(22) PCT Filed: Oct. 4, 2018

(86) PCT No.: PCT/JP2018/037268
§ 371 (c)(1),
(2) Date: Apr. 14, 2020

(87) PCT Pub. No.: WO2019/082621
PCT Pub. Date: May 2, 2019

(65) Prior Publication Data
US 2020/0255788 A1 Aug. 13, 2020

(30) Foreign Application Priority Data

Oct. 25, 2017 (JP) .............................. JP2017-206237
Jul. 31, 2018 (JP) .............................. JP2018-143848

(51) Int. Cl.
*C12M 3/00* (2006.01)
*C12M 1/00* (2006.01)
(Continued)

(52) U.S. Cl.
CPC .............. *C12M 35/02* (2013.01); *C12M 1/42* (2013.01); *C12N 13/00* (2013.01)

(58) Field of Classification Search
CPC ............................... C12M 35/02; C12N 13/00
See application file for complete search history.

(56) References Cited

U.S. PATENT DOCUMENTS

| 4,810,934 A * | 3/1989 | Shimoda ................. H01J 1/135 313/352 |
| 2013/0052711 A1 * | 2/2013 | Chen ...................... C12M 35/02 435/173.6 |

(Continued)

FOREIGN PATENT DOCUMENTS

| JP | S60-110287 A | 6/1985 |
| JP | 2006-325493 A | 12/2006 |
| JP | 2016-136485 A | 7/2016 |

*Primary Examiner* — Nathan A Bowers
(74) *Attorney, Agent, or Firm* — ScienBiziP, P.C.

(57) ABSTRACT

The present invention provides a cell stimulation device capable of uniformly electrically stimulating cells intended to be electrically stimulated, and of preventing medium components from decomposing and depositing.
[Solution] The cell stimulation device according to the present invention is intended to stimulate the cells being cultured in a culture medium, and is characterized in that the cell stimulation device includes an electron emission element for feeding electric charges to the culture medium via a gas phase, and an electric charge collecting electrode for collecting the electric charges from the culture medium, the electron emission element includes a lower electrode, a surface electrode, and an intermediate layer disposed between the lower electrode and the surface electrode, and (Continued)

the electric charge collecting electrode is disposed so as to be contactable with the culture medium.

10 Claims, 7 Drawing Sheets

(51) Int. Cl.
    *C12M 1/42*     (2006.01)
    *C12N 13/00*     (2006.01)

(56) References Cited

U.S. PATENT DOCUMENTS

| | | | |
|---|---|---|---|
| 2014/0111901 A1* | 4/2014 | Chawke | B01J 19/087 |
| | | | 361/226 |
| 2017/0084928 A1* | 3/2017 | Kneule | B29C 45/1671 |
| 2017/0202156 A1* | 7/2017 | Harms | A01G 7/04 |
| 2017/0321331 A1* | 11/2017 | Mitsushima | C01B 3/0005 |

* cited by examiner

CELL STIMULATION DEVICE, CELL CULTURE DEVICE, AND CELL STIMULATION METHOD

TECHNICAL FIELD

The present invention relates to a cell stimulation device, a cell culture device, and a cell stimulation method.

BACKGROUND ART

There has been a known cell culture method in which cultured cells responsive to electric stimulation are electrically stimulated (e.g. see Patent Document 1). In this cell culture method, cell metabolism is enhanced by the electric stimulation to increase a cell proliferation rate.

On the other hand, there has been a known electron emission element which allows electrons to flow into an intermediate layer and emits the electrons by applying a voltage between a lower electrode and a surface electrode (e.g. see Patent Document 2). In addition, there is a known anion generation device which generates oxygen anions by electrons emitted from an electron emission element and ejects these anions to a living body through a gas flow (e.g. see Patent Document 3).

CITATION LIST

Patent Literature

[PTL 1]
Japanese Patent Laid-Open No. 60-110287
[PTL 2]
Japanese Patent Laid-Open No. 2016-136485
[PTL 3]
Japanese Patent Laid-Open No. 2006-325493

SUMMARY OF THE INVENTION

Problems to be Solved by the Invention

In a conventional cell culture method of electrically stimulating cultured cells, at least two electrodes are placed in a culture medium, and a voltage is applied to between the two electrodes. Thereby, electrochemical reaction may be caused on an interface between the electrodes and a culture solution, resulting in electrolysis of water, and decomposition and deposition of components in the culture solution. In addition, a current tends to flow locally into a region with a short distance between the electrodes, and therefore it is difficult to uniformly electrically stimulate the cultured cells intended to be electrically stimulated.

Also, in a conventional anion generation device, since anions are ejected together with a gas, it is difficult to uniformly feed electric charges to cells intended to be electrically stimulated. In addition, there is a problem that water in a culture medium tends to evaporate due to the gas ejected from the anion generation device, and the culture medium is dried. In addition, it is difficult to maintain gas type conditions of an atmosphere gas for culturing cells.

The present invention has been made in view of such circumstances, and the present invention provides a cell stimulation device capable of uniformly electrically stimulating cells intended to be electrically stimulated, and suppressing decomposing and depositing of medium components.

Solution to Problem

The present invention provides a cell stimulation device for stimulating cells being cultured in a culture medium, the cell stimulation device is characterized in that the cell stimulation device includes an electron emission element for feeding electric charges to the culture medium via a gas phase, and an electric charge collecting electrode for collecting the electric charges from the culture medium, the electron emission element includes a lower electrode, a surface electrode, and an intermediate layer disposed between the lower electrode and the surface electrode, and the electric charge collecting electrode is disposed so as to be contactable with the culture medium.

Effect of the Invention

Since the electron emission element included in the cell stimulation device according to the present invention includes the lower electrode, the surface electrode, and the intermediate layer disposed between the lower electrode and the surface electrode, electrons which have passed through the intermediate layer can be emitted from the surface electrode side by applying a voltage to between the lower electrode and the surface electrode. The emitted electrons make it possible to generate electric charges such as oxygen anions in a gas phase between the electron emission element and the culture medium.

Since the electric charge collecting electrode included in the cell stimulation device according to the present invention is disposed so as to come into contact with the culture medium for culturing cells, the electrons can flow from the culture medium to the electric charge collecting electrode. Thereby, a potential difference between the electric charge collecting electrode and the culture medium can be decreased. In addition, an electric field can be generated in a gas phase between the surface electrode of the electron emission element and the surface of the culture medium by applying a voltage to the electron emission element or the electric charge collecting electrode. The generated anions can be transported to the surface of the culture medium along a line of an electric force (gradient of field intensity) in this electric field, and the anions can be fed to the culture medium. The cells being cultured in the culture medium can be electrically stimulated by the anions. In addition, since the anions flow to the electric charge collecting electrode, the culture medium can be suppressed being electrically charged. In addition, in the cell stimulation device according to the present invention, the anions are fed to the culture medium by using the electric field generated in the gas phase, and therefore a gas flow mechanism of nitrogen gas and argon gas is not required. Thus, there is no concern about dried culture medium and floating cells during the electric stimulation of the cells, and a gas composition in a culture atmosphere is not affected.

Since the electron emission element included in the cell stimulation device according to the present invention can emit electrons from a surface of the surface electrode, anions can be uniformly generated in the gas phase between the surface of the culture medium and the surface electrode. Thereby, anions can also be uniformly fed to the culture medium positioned under the surface electrode, and the cells positioned under the surface electrode can be uniformly electrically stimulated.

In the cell stimulation device according to the present invention, electric charges generated by the electron emission element are fed to the culture medium via the gas phase, and therefore only the electric charge collecting electrode comes into contact with the culture medium. Thereby, water contained in the culture medium can be prevented from being electrolyzed. In addition, since the electric charge collecting electrode is positively polarized, mineral components ($K^+$, $Ca^{2+}$, $Na^+$, $Mg^{2+}$, and the like) in the culture medium can be prevented from depositing on the electric charge collecting electrode, and a component composition in the culture medium can be prevented from changing.

MODE FOR CARRYING OUT THE INVENTION

The cell stimulation device according to the present invention is intended to stimulate cells being cultured in a culture medium, and is characterized in that the cell stimulation device includes an electron emission element for feeding electric charges to the culture medium via a gas phase, and an electric charge collecting electrode for collecting the electric charges from the culture medium, the electron emission element includes a lower electrode, a surface electrode, and an intermediate layer disposed between the lower electrode and the surface electrode, and the electric charge collecting electrode is disposed so as to be contactable with the culture medium.

Each of the lower electrode and the surface electrode included in the electron emission element has a plurality of elongated electrodes, and the lower electrodes and the surface electrodes are preferably arranged in a lattice shape such that either the lower electrodes or the surface electrodes are arranged in rows, and the others are arranged in columns. Such a configuration makes it possible to emit electrons from any intersection points between the lower electrodes and the surface electrodes to electrically stimulate only cells at target positions in the culture medium. In addition, the cells in the culture medium can be electrically stimulated while an electric stimulatory level is desirably distributed.

Preferably, the cell stimulation device according to the present invention includes a power supply. Preferably, the power supply is disposed such that a voltage can be applied to between the lower electrode and the surface electrode. Thereby, an electric field can be generated on the intermediate layer, electrons can be allowed to flow into the intermediate layer by this electric field, and the electrons can be emitted from the surface electrode. In addition, anions can be generated in a gas phase by these electrons. In addition, preferably the power supply is disposed such that a potential difference can be generated between the electron emission element and the electric charge collecting electrode. Thereby, an electric field can be generated between the surface electrode and a surface of the culture medium, and anions can be transported to the culture medium by this electric field.

Preferably, the power supply is electrically connected to the electron emission element and the electric charge collecting electrode such that a current generated in the gas phase by feeding the electric charges from the electron emission element to the culture medium, and a current generated in the culture medium by a collecting the electric charges from the culture medium by the electric charge collecting electrode become a loop current. Thereby, the electric charges can be efficiently fed to the culture medium to properly stimulate the cells.

Preferably, the cell stimulation device according to the present invention includes an insulating member, and a needle-like terminal fixed to the insulating member. In addition, preferably, the electron emission element is fixed to the insulating member. Furthermore, preferably, the needle-like terminal is in contact with the lower electrode at the tip of the terminal. Such a configuration makes it possible to apply the voltage to the lower electrode via the needle-like terminal. In addition, poor contact between the needle-like terminal and the lower electrode can be prevented.

Preferably, the electric charge collecting electrode included in the cell stimulation device according to the present invention is fixed to the insulating member. Such a configuration makes it possible to bring the electric charge collecting electrode into contact with the culture medium when the insulating member is disposed above the culture medium.

The present invention also provides a cell culture device including the cell stimulation device according to the present invention and a culture container for containing the culture medium. The cell stimulation device includes the insulating member. The electron emission element is fixed to the insulating member. The insulating member is disposed on the culture container such that the surface electrode is opposite to the surface of the culture medium with the gas phase interposed therebetween.

Preferably, the insulating member is disposed such that a distance between the surface electrode and the surface of the culture medium is 0.5 to 3 mm. Thereby, anions generated in the gas phase can be easily fed to the culture medium.

Preferably, the electric charge collecting electrode is fixed to the culture container. Thereby, a leak current is prevented from flowing between the electric charge collecting electrode and the electron emission element.

Also, the present invention provides a cell stimulation method including a step for feeding electric charges to the culture medium for culturing the cells, via the gas phase, by applying a voltage to between the lower electrode and the surface electrode of the electron emission element including the lower electrode, the surface electrode, and the intermediate layer disposed between the lower electrode and the surface electrode. The electric charge-feeding step is intended to feed the electric charges by using the electric field between the electron emission element and the culture medium.

Hereinafter, the present invention will be explained in more detail with reference to a plurality of embodiments. Configurations presented in the figures and the following description are merely examples, and the scope of the present invention is not limited to constituents presented in the figures and the following description.

First Embodiment

Figure 1:
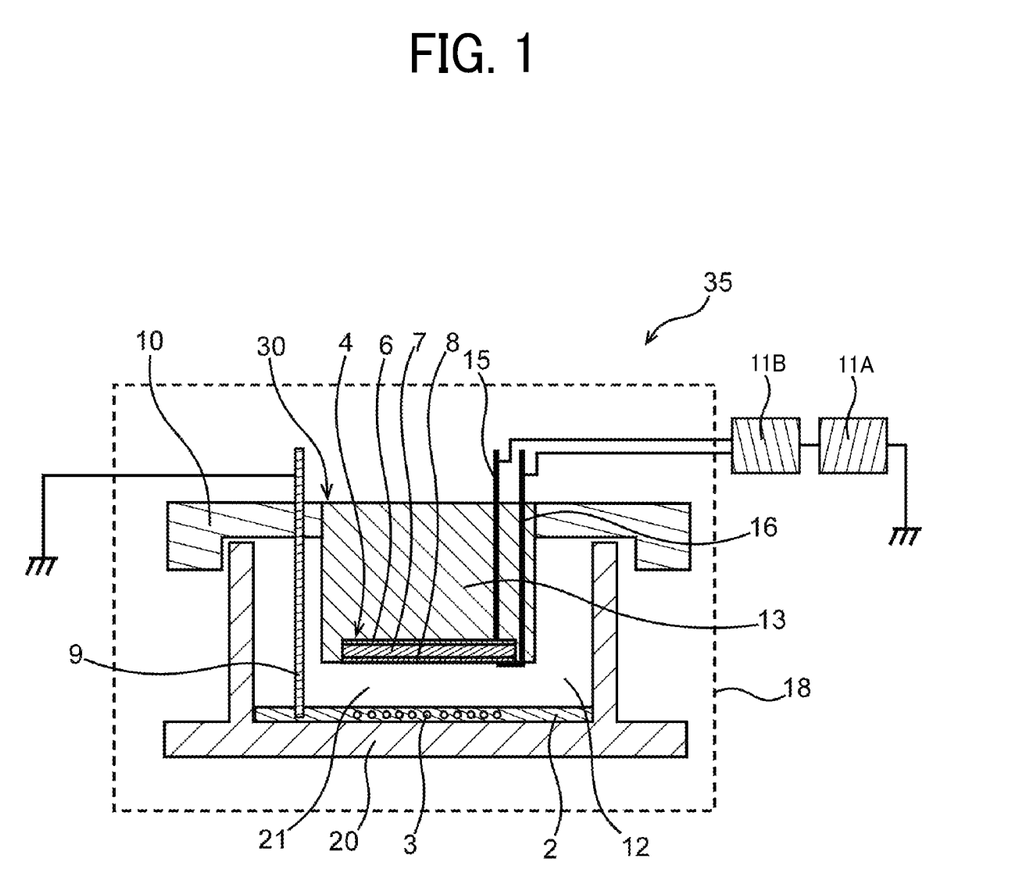
FIG. 1 is a schematic sectional view of a cell culture device according to an embodiment of the present invention.
Figure 2:
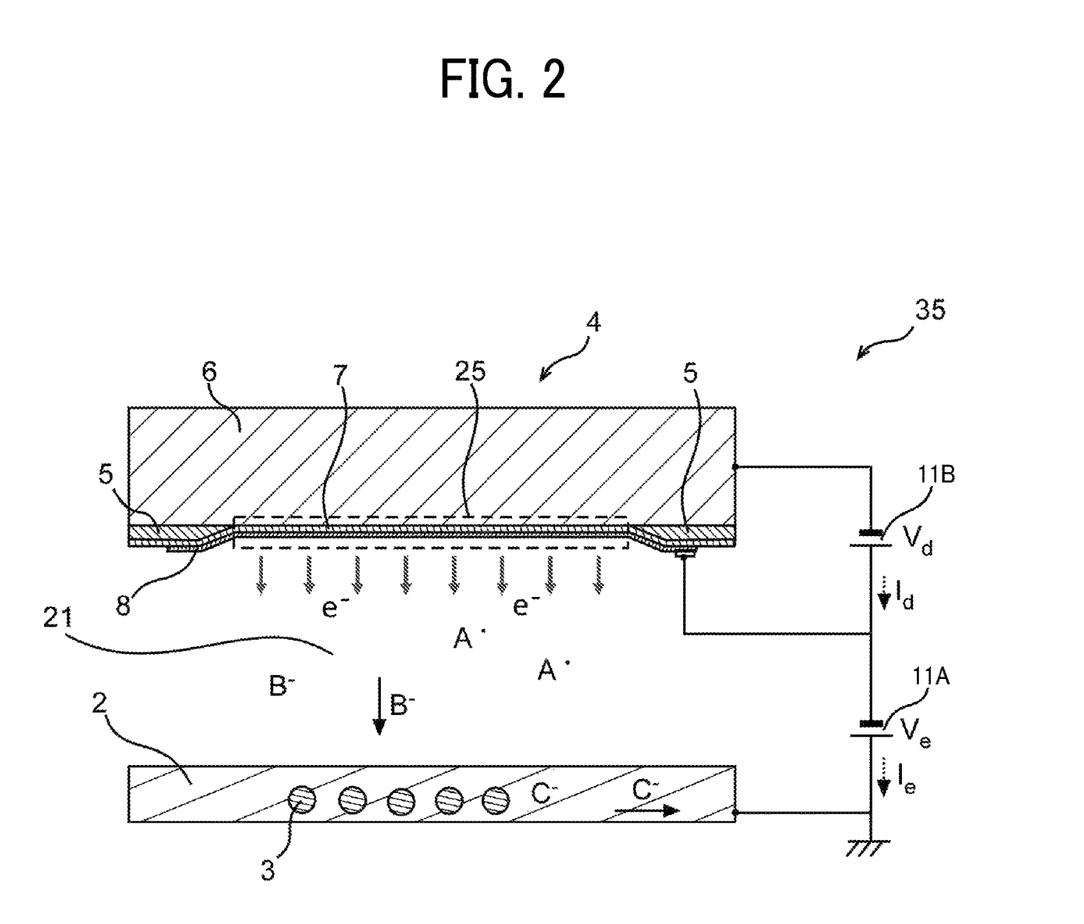
FIG. 2 is a schematic circuit diagram of the cell culture device according to an embodiment of the present invention.

FIG. 1 is a schematic sectional view of a cell culture device 35 including a cell stimulation device 30 according to the first embodiment, and FIG. 2 is a schematic circuit diagram of the cell culture device 35.

The cell stimulation device 30 according to the first embodiment is intended to stimulate cells 3 being cultured in a culture medium 2, and is characterized in that the cell stimulation device 30 includes an electron emission element 4 for feeding electric charges to the culture medium 2 via a gas phase 21, and an electric charge collecting electrode 9 for collecting the electric charges from the culture medium 2, the electron emission element 4 includes a lower electrode 6, a surface electrode 8, and an intermediate layer 7 disposed between the lower electrode 6 and the surface electrode 8, and the electric charge collecting electrode 9 is disposed so as to be contactable with the culture medium 2.

The cell culture device 35 according to the first embodiment includes the cell stimulation device 30 according to the first embodiment and a culture container 20 for containing the culture medium 2.

The cell stimulation method according to the first embodiment includes a step for feeding the electric charges to the culture medium 2 for culturing the cells 3, via the gas phase 21, by applying a voltage between the lower electrode 6 and the surface electrode 8 of the electron emission element 4 including the lower electrode 6, the surface electrode 8, and the intermediate layer 7 disposed between the lower electrode 6 and the surface electrode 8. The electric charge-feeding step is intended to feed the electric charges by using an electric field between the electron emission element 4 and the culture medium 2.

In this specification, the electric charges includes electrons, ions in gas phase, and ions in liquid.

Hereinafter, the cell stimulation device 30, the cell culture device 35, and a cell stimulation method according to the first embodiment will be explained.

The cell stimulation device 30 is intended to electrically stimulate the cells 3 being cultured in the culture medium 2 for the purpose of proliferation, induction differentiation, or the like of the cells.

Examples of the cells 3 to be cultured in the culture medium 2 include cells and tissues of multicellular organisms, transgenic cells, gene recombinant cells, and microbes. The cells 3 can be cells responsive to electric stimulation. Examples of the electric stimulation-responsive cells include muscle cells, nerve cells, osteoblasts, osteoclasts, chondrocytes, osteocytes, and fibroblasts.

In addition, as the cells 3 to be cultured in the culture medium 2, preliminary cultured cells can be used. In addition, the preliminary cultured cells can be seeded in the culture medium 2 such that the cells 3 are contained in the culture medium 2 at a rate of $10^3$ to $10^6$ cells/cm$^2$.

The culture medium 2 provides a growth environment to the cells 3. The culture medium 2 can be used without any particular limitation as long as it is a commonly used cell culture medium. The culture medium 2 may be a liquid culture medium, or a solid culture medium prepared by solidifying a liquid culture using a gelling agent such as agar. In addition, the culture medium 2 may be a combination of a liquid culture medium and a solid culture medium. Examples of the culture medium 2 include MEM medium (Eagle's minimum essential medium), D-MEM medium (Dulbecco's modified eagle's medium), α-MEM medium (α-modified Eagle's minimum essential medium), GMEM (Glasgow's minimum essential medium), Ham's F-12 (nutrient mixture F-12 Ham), IMDM (Iscove's modified Dulbecco's medium), RPMI-1640 medium, D-PBS (Dulbecco's phosphate-buffered saline), and HBSS (Hanks's balanced salt solution).

The culture medium 2 is contained in the culture container 20. Examples of the culture container 20 include a multi-well plate including a plurality of wells 12, and a culture dish. In addition, the cell culture device 35 can be formed by combining the culture container 20 with the cell stimulation device 30. As a material of the culture container 20, an existing material such as a glass or a plastic can be used. The culture container 20 is preferably a container of which the bottom surface is subjected to surface treatment suitable for fixing the cells 3. The surface treatment can be a commonly known treatment for applying a matrix protein, a collagen, fibronectin, laminin, or the like to the bottom surface of the container. The cell culture device 35 can be disposed in an inverter 18. Thereby, a temperature, an atmospheric gas, and the like of the culture medium 2 can be controlled, so that the cells 3 can be stably cultured. A culture atmosphere is e.g. air of temperature: 37° C., relative humidity: 95%, and atmosphere gas: 5% carbon dioxide gas.

The cell stimulation device 30 includes the electron emission element 4 for feeding the electric charges to the culture medium 2 via the gas phase 21. The electron emission element 4 is planar and can emit electrons. The electron emission element 4 includes the lower electrode 6, the surface electrode 8, and the intermediate layer 7 disposed between the lower electrode 6 and the surface electrode 8. In addition, a power supply 11b can generate an electric field in the intermediate layer 7 by applying a voltage to between the surface electrode 8 and the lower electrode 6. This electric field allows electrons to flow through the intermediate layer 7 to emit the electrons from the surface electrode 8 of the electron emission element 4. The electrons generate electric charges such as oxygen anions in the gas phase 21. In addition, the culture medium 2 is irradiated with the anions.

For example, a rectangular wave AC voltage with a peak value of $14V_{0-p}$ to $24V_{0-p}$ and a frequency of 500 to 10000 Hz is applied to between the surface electrode 8 and the lower electrode 6 by the power supply 11b. In addition, an on/off duty ratio can be variable from 1 to 100%.

In addition, an ion irradiation dose from the electron emission element 4 can be 0.5 to 5.0 µA/cm$^2$.

If the ion irradiation dose is lower than 0.5 µA/cm$^2$, the culture speed is slow, and if the ion irradiation dose is higher than 5.0 µA/cm$^2$, a possibility of cell death is high, and the culture speed is slow.

In addition, for the purpose of regulating the ion irradiation dose during driving to almost constant (fluctuation range is ±10% or less, preferably ±5% or less) and satisfying the irradiation dose, the irradiation dose can be controlled using the drive voltage peak value or the rectangular wave duty ratio as a parameter.

The culture can be stably advanced by regulating the ion irradiation dose to almost constant.

The surface electrode 8 is positioned on the surface of the electron emission element 4. The surface electrode 8 can have a thickness of 5 to 100 nm, preferably 40 to 100 nm. In addition, examples of a material of the surface electrode 8 include gold and platinum. Thereby, the surface electrode 8 can be prevented from being oxidized due to autoclave sterilization or the like. In addition, the surface electrode 8 may be composed of a plurality of metal layers.

Even when the surface electrode 8 has the preferable thickness of 40 nm or larger, the surface electrode 8 may have a plurality of openings, gaps, and a thinned portion having a thickness of 10 nm or smaller. The electrons which have passed through the intermediate layer 7 can pass or penetrate the openings, the gaps, and the thinned portion, and the electrons can be emitted from the surface electrode 8. Such openings, gaps, and thinned portion can be formed by applying a voltage to between the lower electrode 6 and the surface electrode 8 (forming process, initial voltage application).

The lower electrode 6 is opposite to the surface electrode 8 via the intermediate layer 7. The lower electrode 6 may be a metal plate, or a plate made of an insulator having a metal layer or a conductor layer. In addition, when the lower electrode 6 is made of a metal plate, this metal plate may be a substrate of the electron emission element 4. Examples of a material of the lower electrode 6 include aluminum, stainless steel, and nickel. The lower electrode has a thickness of e.g. 200 µm to 1 mm.

The intermediate layer 7 refers to a layer through which the electrons flow by the electric field formed by applying the voltage to the surface electrode 8 and the lower electrode 6. The intermediate layer 7 may be semiconductive. The intermediate layer 7 contains at least one of an insulating resin, a conductive resin, and an insulating fine particle. In addition, the intermediate layer 7 preferably includes a conductive fine particle. The intermediate layer 7 can have a thickness of 1 to 1.8 µm. Since the electrons which have passed through the intermediate layer 7 are emitted from the surface electrode 8, the electron emission element 4 can emit the electrons from the surface of the surface electrode 8. Thereby, the electrons can be uniformly emitted to the gas phase 21 on the surface electrode 8, so that the electrons can generate electric charges such as oxygen anions.

The electron emission element 4 may have an insulating layer 5 between the surface electrode 8 and the lower electrode 6. This insulating layer 5 can have openings. The openings of the insulating layer 5 are formed so as to correspond to regions where the electrons should be emitted in the surface electrode. Since the electrons cannot flow through the insulating layer 5, the electrons flow through the intermediate layer 7 corresponding to the openings of the insulating layer 5, and the electrons are emitted from the surface electrode 8. Thus, electron emission regions can be formed on the surface electrode 8 by disposing the insulating layer 5.

The electron emission element 4 can be detachably fixed to an insulating member 13. Disposition of this insulating member 13 on the culture container 20 makes it possible to dispose the electron emission element 4 such that the surface electrode 8 of the electron emission element 4 is opposite to the surface of the culture medium 2 in the culture container 20 via the gas phase 21. Such a disposition of the electron emission element 4 makes it possible to generate electric charges such as oxygen anions in the gas phase 21 between the electron emission element 4 and the culture medium 2, from the electrons emitted from the side of the surface electrode 8 of the electron emission element 4. In addition, the electron emission element 4 can be disposed such that the surface electrode 8 and the surface of the culture medium 2 are substantially parallel to each other.

The insulating member 13 may be integrated with a cover member 10. In this case, the insulating member 13 can be disposed so as to project from the cover member 10 toward the culture medium 2 (in well 12). In addition, the electron emission element 4 can be fixed to an end surface of the insulating member 13 projecting from the cover member 10 so as to be parallel to the surface of the culture medium 2.

Preferably, materials of the insulating member 13 and the cover member 10 are a heat-resistant PEEK material or a fluorine-based material. A member facing the cells is previously sterilized using an autoclave. Since the sterilization is carried out with high-temperature steam at higher than 150° C., the member should be resistant against repetitive thermal deformation of the material.

The cover member 10 is disposed so that the cell stimulation device 30 can be put on the culture container 20. In addition, the cover member 10 can have an insulation property.

The insulating member 13 or the cover member 10 can be disposed such that a distance between the surface electrode 8 and the surface of the culture medium 2 is 0.5 mm to 3 mm. Thereby, the anions generated in the gas phase 21 can be easily fed to the culture medium 2. The distance between the surface electrode 8 and the surface of the culture medium 2 can be preferably 1 mm to 2 mm.

For example, the distance between the surface electrode 8 and the surface of the culture medium 2 can be adjusted by adjusting a depth of the well of the culture container 20, a depth of the culture medium 2, a height of the insulating member 13 projecting from the cover member 10, and the like.

As described above, when the electron emission element 4 is opposite to the surface of the culture medium 2 via the gas phase 21, it is possible to prevent inhibition of the oxygen gas feeding from the gas phase 21 to the culture medium 2. Thereby, a dissolved oxygen content in the culture medium 2 can be maintained.

In addition, detachable fixation of the electron emission element 4 to the insulating member 13 facilitates exchange of the electron emission element 4.

The cell stimulation device 30 can have a first terminal 15 and a second terminal 16 which are fixed to the insulating member 13. Each of the first terminal 15 and the second terminal 16 has a contact point in contact with the electron emission element 4. When the electron emission element 4 is attached to the insulating member 13, the first terminal, the second terminal, and the electron emission element 4 can be disposed such that the first terminal 15 is electrically connected to the lower electrode 6, and the second terminal 16 is electrically connected to the surface electrode 8. A voltage can be applied to between the surface electrode 8 and the lower electrode 6 via the first and second terminals.

The electric charge collecting electrode 9 is disposed so as to come into contact with the culture medium 2 for culturing the cells 3. Thereby, the electrons can flow from the culture medium 2 to the electric charge collecting electrode 9, so that a potential of the electric charge collecting electrode 9 and a potential of the culture medium 2 can be equal or almost equal to each other. For example, when the electric charge collecting electrode 9 is grounded, the culture medium 2 can be prevented from being electrically charged.

In the cell stimulation device 30 according to the first embodiment, electric charges generated by the electron emission element 4 are fed to the culture medium 2 via the gas phase 21, and therefore, among the electrodes, only the electric charge collecting electrode 9 comes into contact with the culture medium 2. Thereby, water contained in the culture medium 2 can be prevented from being electrolyzed. In addition, since the electric charge collecting electrode 9 is positively polarized, mineral components ($K^+$, $Ca^{2+}$, $Na^+$, $Mg^{2+}$, and the like) in the culture medium 2 do not deposit on the electric charge collecting electrode 9, and a component composition of the culture medium 2 can be prevented from changing.

The electric charge collecting electrode 9 can be fixed to e.g. the insulating member 13 or the cover member 10. When the insulating member 13 and the cover member 10 are placed on the culture container 20, the electric charge collecting electrode 9 can be disposed so as to come into contact with the culture medium 2.

The electric charge collecting electrode 9 has a shape of e.g. a rod, a flat plate, a mesh, or a punching metal. In addition, the electric charge collecting electrode 9 may have a structure in which a flat plate, a mesh, or a punching metal is attached to a tip of a rod. The flat plate, the mesh, or the punching metal attached to the tip of the rod in the electric charge collecting electrode 9 can be disposed at a bottom of the well 12 such that the cells 3 are positioned between the electric charge collecting electrode 9 and the electron emission element 4. With such a configuration, anions generated on the surface of the culture medium 2 by electron emission of the electron emission element 4 flow toward the bottom of the well 12. Thus, the cells 3 being cultured in the culture medium 2 can be electrically stimulated with high efficiency.

An electric field can be generated in the gas phase 21 between the surface electrode 8 of the electron emission element 4 and the surface of the culture medium 2 by applying a voltage to the electron emission element 4 or the electric charge collecting electrode 9 by the power supply 11a. Anions generated by emission of electrons from the electron emission element 4 can be transported to the surface of the culture medium 2 (a current can be allowed to flow through the gas phase 21) along a line of an electric force (gradient of field intensity) in the electric field of the gas phase 21, so that anions ($OH^-$, $Cl^-$, $O_2^-$, and the like) can be generated in the culture medium 2. The cells 3 being cultured in the culture medium 2 can be electrically stimulated by the anions. In addition, since the anions move through the culture medium 2 and flow to the electric charge collecting electrode 9 (a current flows through the culture medium 2), the culture medium 2 can be prevented from being electrically charged.

For example, the electric charge collecting electrode 9 is grounded, and a DC voltage of −1000 to −50 V can be applied to between the electron emission element 4 and the ground by the power supply 11a. In addition, an interval between the surface electrode 8 of the electron emission element 4 and the surface of the culture medium 2 can be 0.5 mm to 3 mm (preferably 1 mm to 2 mm). Since the electric charge collecting electrode 9 is grounded, the potential of the culture medium 2 is approximately 0 V, and a potential of the surface electrode 8 is −1000V to −50 V. Also, since the interval between the culture medium 2 and the surface electrode 8 is 0.5 mm to 3 mm, an electric field with a strong field intensity can be generated in the gas phase 21 between the culture medium 2 and the surface electrode 8. Anions generated by emitting electrons from the electron emission element 4 can be fed to the culture medium 2 using this electric field.

The power supplies 11a and 11b are electrically connected to the electron emission element 4 and the electric charge collecting electrode 9 such that a current generated in the gas phase 21 by feeding electric charges from the electron emission element 4 to the culture medium 2, and a current generated in the culture medium 2 by collecting the electric charges from the culture medium 2 by the electric charge collecting electrode 9 become a loop current.

For example, as illustrated in FIG. 1 and FIG. 2, an electric field generated by applying a voltage Ve to between the surface electrode 8 and the electric charge collecting electrode 9 using the power supply 11a allows ions B- (ions B- are generated in the gas phase 21 by electrons emitted from the surface electrode 8) to move through the gas phase 21, and thereby, a current is generated in the gas phase 21.

The ions B- reaches the culture medium 2, dissolves in the culture medium 2, stimulates signaling systems related to formation of various constituents for cells, and finally, as ions C- (ions C- are the ions B- themselves, and/or other ion species derived from the ions B-), moves to the electric charge collecting electrode 9, to generate a current in the culture medium 2.

Thus, a loop current can be allowed to flow through the circuit including the power supply 11a, the surface electrode 8, the gas phase 21, and the culture medium 2.

Since the electron emission element 4 can emit electrons from the surface of the surface electrode 8, anions can be uniformly generated in the gas phase 21 between the surface of the culture medium 2 and the surface electrode 8. Since the anions can be fed to the culture medium 2 by the electric field, anions can also be uniformly generated in the culture medium 2 positioned under the surface electrode 8, and the cells 3 positioned under the surface electrode 8 can be uniformly electrically stimulated. Thereby, the cells intended to be electrically stimulated can be uniformly electrically stimulated.

The electric stimulation (ion irradiation) by the cell stimulation device 30 can be started e.g. at the timing when the seeded cells begin to divide.

In addition, the culture medium 2 where the cells 3 are fixed can be irradiated with ions by setting an irradiation dose, an irradiation interval, and an irradiation timing suitable for the cell type.

A period for emitting electrons from the electron emission element 4 (period for applying a voltage by the power supplies 11a and 11b) can be set within a range of e.g. 5 seconds to 1 minute.

Second Embodiment

Figure 3:
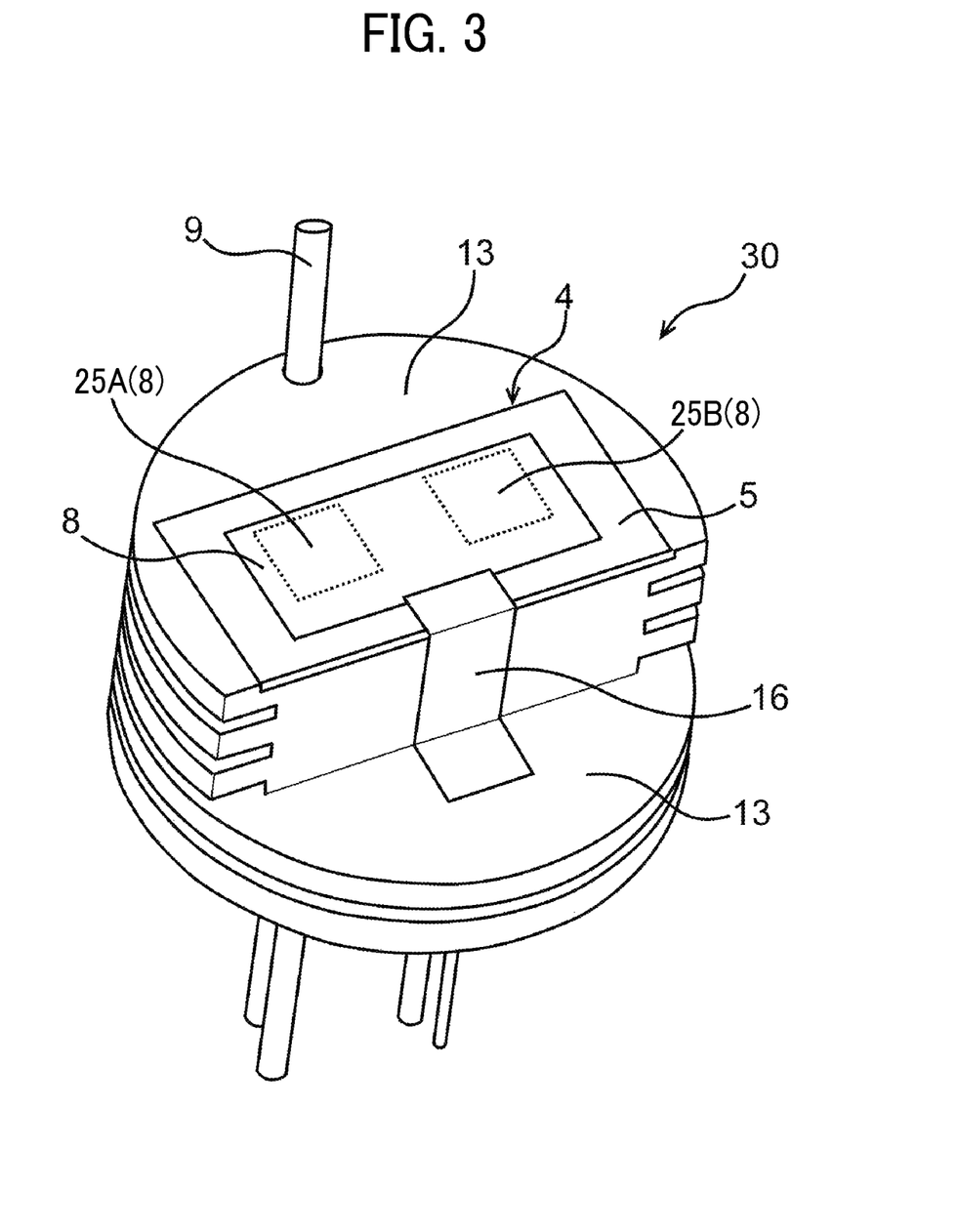
FIG. 3 is a schematic perspective view of a cell stimulation device according to an embodiment of the present invention.
Figure 4:
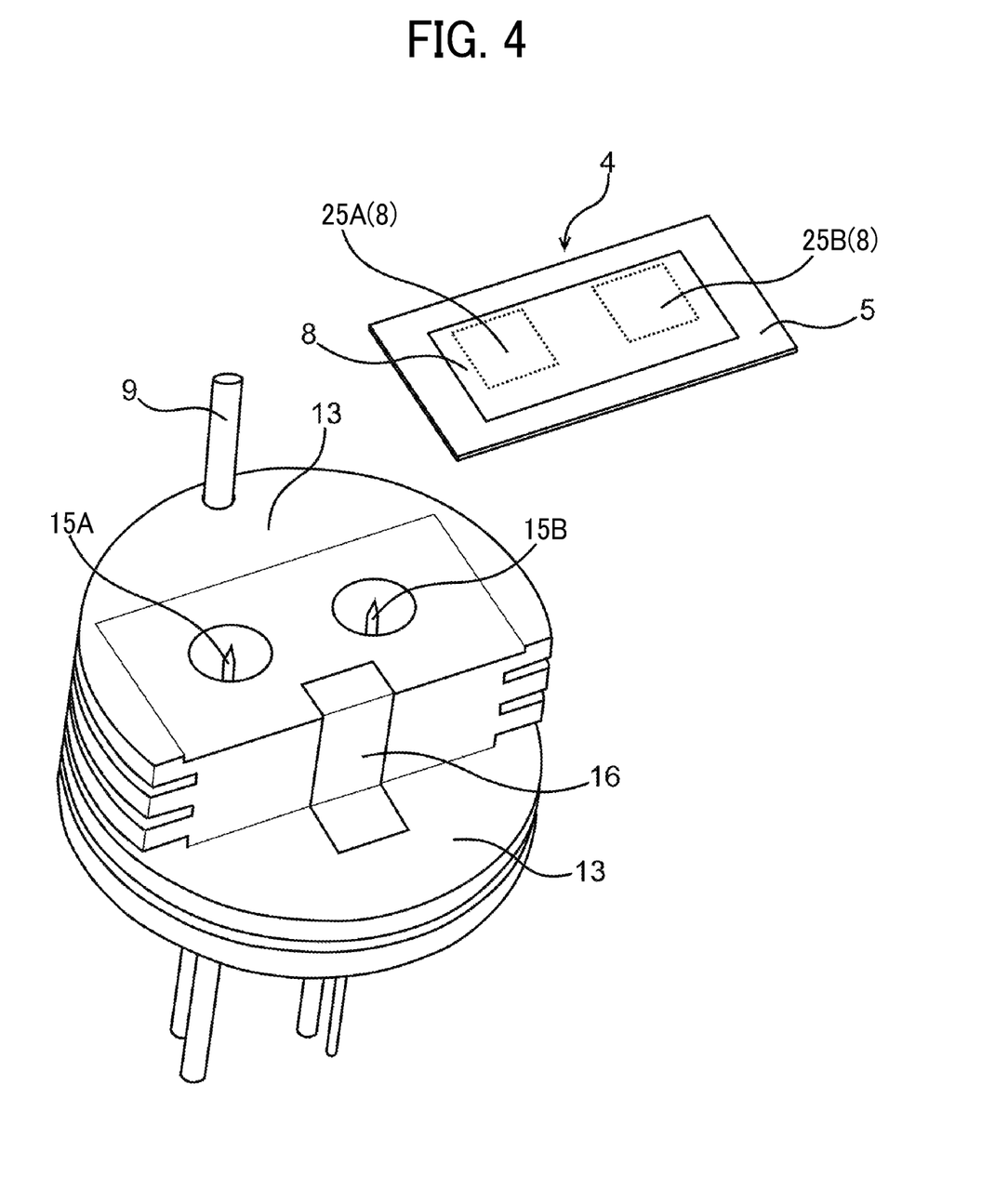
FIG. 4 is a schematic exploded view of the cell stimulation device according to an embodiment of the present invention.

FIG. 3 is a schematic perspective view of a cell stimulation device 30 according to the second embodiment, and FIG. 4 is a schematic exploded view of the cell stimulation device 30 according to the second embodiment.

In the second embodiment, the electron emission element 4 included in the cell stimulation device 30 as illustrated in FIG. 3 is disposed so as to be detachable from the insulating member 13 as in the exploded view of FIG. 4.

In the electron emission element 4, the intermediate layer 7 and the surface electrode 8 are laminated on a metal plate as a lower electrode 6. For example, the lower electrode 6 is a 12×24 mm rectangle metal plate having a thickness of 0.5 mm. In addition, examples of the material of the lower electrode 6 include aluminum, stainless steel, and nickel. In addition, the intermediate layer 7 has a thickness of e.g. 1.0 to 1.8 μm.

In addition, the insulating layer 5 having openings on portions having electron emission regions 25 is laminated between the lower electrode 6 and the surface electrode 8. Since no current flows through the insulating layer 5, the electrons are emitted only from the electron emission regions 25 of the surface electrode 8 corresponding to the openings of the insulating layer 5. The openings of the insulating layer 5 can have a shape of e.g. a 5 mm square. For the insulating layer 5, an inorganic material such as a metal oxide and a metal nitride, or an organic material such as a silicone-based resin and a phenol-based resin can be used.

The surface electrode 8 can have a thickness of 40 to 100 nm. Thereby, electrons which have passed through the intermediate layer 7 can be emitted from the electron emission regions 25 of the surface electrode 8 corresponding to the openings of the insulating layer 5. For example, the surface electrode 8 can be 18×8.5 mm rectangle in size. In addition, the electron emission regions can be 5 mm square in size. The material of the surface electrode 8 is e.g. gold or platinum.

First terminals 15a and 15b are disposed in openings formed on the insulating member 13 and have a needle shape, and the tips of the first terminals 15a and 15b serve as contact points with the rear surface of the lower electrode 6 of the electron emission element 4. Thereby, a voltage can be applied to the lower electrode 6 via the first terminals 15. In addition, contact failure between the first terminals 15 and the lower electrode 6 can be prevented by using the tips of the first terminals 15 as contact points. Also, the first terminals 15 may be spring type needle-like terminals. Thereby, contact failure between the first terminals 15 and the lower electrode 6 can be prevented.

Normally, the cell stimulation device 30 is sterilized using an autoclave before culturing the cells 3 in the cell culture device 35. Since the autoclave sterilization is carried out with high-temperature steam, this treatment may form a thin oxide film on a surface of a metal member (e.g. metal plate serving as the lower electrode 6) included in the cell stimulation device 30. This oxide film may cause the contact failure. When the tips of the needle-like first terminals 15 are used as contact points, the tips can penetrate the oxide film to reliably secure electric conduction between the first terminals 15 and the lower electrode 6.

The second terminal 16 is disposed so as to fix the electron emission element 4 to the insulating member 13 and comes into contact with the surface electrode 8 of the electron emission element 4. Thereby, a voltage can be applied to the surface electrode 8 via the second terminal 16. In addition, the second terminal 16 and the first terminals 15 may be metal plates of which the surfaces have a gold plating layer. Thereby, formation of an oxide film on the surface of the second terminal 16 due to the autoclave sterilization can be prevented, and also poor contact can be prevented.

The insulating member 13 has a slit structure on its surface. This makes it possible to prevent a leakage current (edge leakage) from occurring between the electric charge collecting electrode 9 and a metal member electrically connected to the electrode 9 and between the electron emission element 4 and a metal member electrically connected to the element 4.

Other configurations are the same as in the first embodiment. Also, the description about the first embodiment applies to the second embodiment unless no inconsistency occurs. Also, the slit structure on the surface of the insulating member 13 can apply to other structures in the first embodiment or the like.

In the second embodiment, the electron emission element 4 is rectangular (electron emission regions 25a and 25b are square), but may be another shape such as a circle and a star depending on the situation. As an example, the electron emission element 4 can be a shape coinciding with the shape of the culture medium 2 (however, since the electron emission element 4 cannot come into contact with the electric charge collecting electrode 9, the contacting portion has a chipped shape) for the purpose of using the culture medium 2 as efficiently as possible.

Third Embodiment

Figure 5:
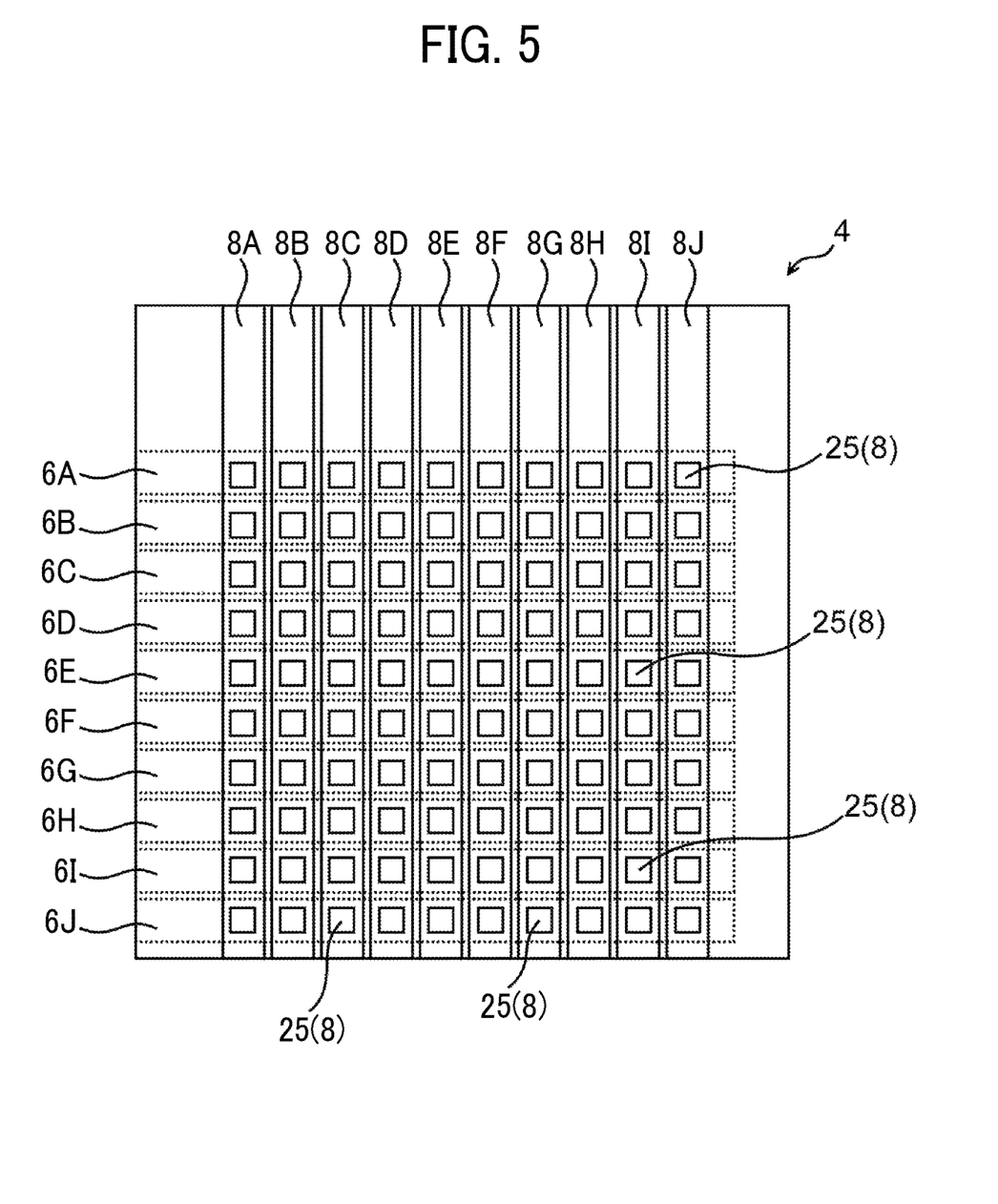
FIG. 5 is a schematic top view of an electron emission element included in the cell stimulation device according to an embodiment of the present invention.

FIG. 5 is a schematic top view of the electron emission element 4 included in the cell stimulation device 30 according to the third embodiment.

The lower electrode 6 included in the electron emission element 4 is composed of a plurality of elongated electrodes, e.g. electrodes 6a to 6j in FIG. 5. The electrodes 6a to 6j can be arranged to be parallel to each other. The electrodes 6a to 6j may be e.g. metal layers or conductor layers formed on an insulating substrate. Thereby, the electrodes 6a to 6j can be electrically separated. In addition, different terminals can be individually connected to the electrodes 6a to 6j.

The surface electrode 8 included in the electron emission element 4 is composed of a plurality of elongated electrodes, e.g. electrodes 8a to 8j in FIG. 5. The electrodes 8a to 8j can be arranged to be parallel to each other. The electrodes 8a to 8j may be e.g. metal layers or conductor layers formed on the intermediate layer 7. In addition, different terminals can be individually connected to the electrodes 8a to 8j.

The lower electrode 6 and the surface electrode 8 are arranged in a lattice shape such that either the electrodes 6a to 6j or the electrodes 8a to 8j are arranged in rows, and the others are arranged in columns. In addition, the insulating layer 5 having the openings at positions where the electrodes 6a to 6j and the electrodes 8a to 8j intersect with each other is laminated between the lower electrode 6 and the intermediate layer 7. Thereby, the electron emission regions 25 can be formed on the surface electrode 8 at positions where the electrodes 6a to 6j and the electrodes 8a to 8j intersect with each other (positions corresponding to the openings of the insulating layer 5). These electron emission regions 25 are arranged in a matrix.

By changing the combination of the electrodes 6a to 6j and the electrodes 8a to 8j to which a voltage is applied, electrons are not emitted from one or some of the plurality of electron emission regions 25 arranged in the matrix, and electrons can be emitted from the other electron emission regions 25. For examples, once a voltage is applied only to between the electrodes 6a to 6e and the electrodes 8a to 8e, electrons are emitted to the electron emission regions 25 at intersection points between these electrodes, but no electrons are emitted to the other electron emission regions 25. Thus, it is possible to electrically stimulate only cells in the culture medium positioned below the electron emission regions 25 from which electrons are emitted. That means, only the cells 3 present in the selected regions in the culture medium 2 can be electrically stimulated.

Emission quantities of electrons can be varied among the plurality of electron emission regions 25 arranged in the matrix by varying applied voltages depending on the combination of the electrodes 6a to 6j and the electrodes 8a to 8j. For example, an AC voltage with a peak value of 20 V can be applied to between the electrodes 6a to 6e and the electrodes 8a to 8e, an AC voltage with a peak value of 10 V can be applied to between the electrodes 6f to 6j and the electrodes 8f to 8j, so that a potential difference of 15 V can be applied to between the electrodes 6a to 6e and the electrodes 8f to 8j, and between the electrodes 6f to 6j and the electrodes 8a to 8e. In this case, a quantity of electrons emitted from the electron emission regions 25 at the intersection points between the electrodes 6a to 6e and the electrodes 8a to 8e is relatively large, and a quantity of electrons emitted from the electron emission regions 25 at the intersection points between the electrodes 6f to 6j and the electrodes 8f to 8j is relatively small. In addition, the quantities of electrons emitted from the electron emission regions 25 at the intersection points between the electrodes 6a to 6e and the electrodes 8f to 8j, and electrons emitted from the electron emission regions 25 at the intersection points between the electrodes 6f to 6j and the electrodes 8a to 8e are moderate. An intensity of the electric stimulation applied to the cells 3 in the culture medium 2 also changes depending on these electron emission quantities. Thus, the cells 3 in the culture medium 2 can be electrically stimulated with a desired distribution of the electric stimulatory level. In addition, a screening test can be performed by changing the electric stimulatory level in one well 12.

Other configurations are the same as in the first or second embodiment. Also, the description about the first or second embodiment applies to the third embodiment unless no inconsistency occurs.

Fourth Embodiment

Figure 6:
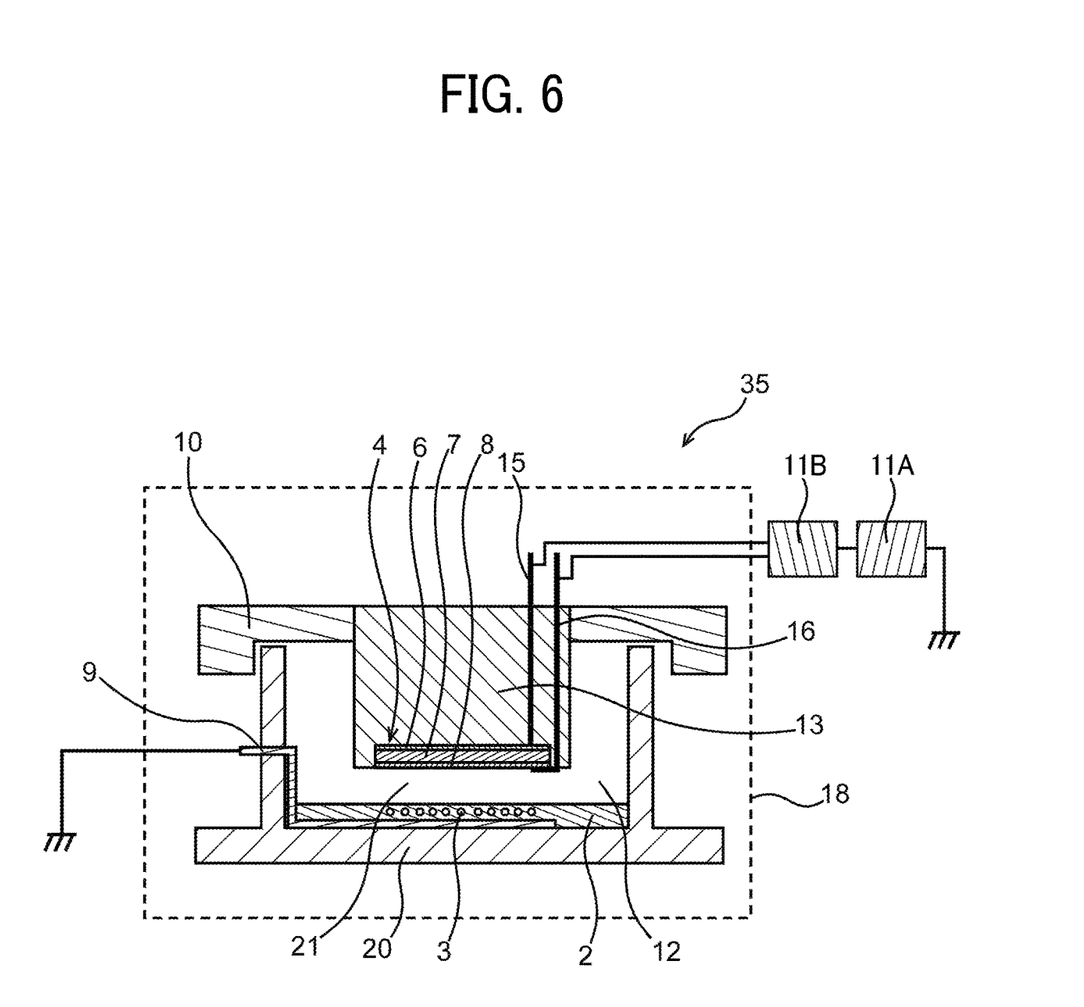
FIG. 6 is a schematic sectional view of the cell culture device according to an embodiment of the present invention.

FIG. 6 is a schematic sectional view of the cell culture device 35 according to the fourth embodiment.

In the fourth embodiment, the electric charge collecting electrode 9 is fixed to the culture container 20. On the other hand, the electron emission element 4 is fixed to the insulating member 13. Such a configuration makes it possible to prevent a leak current from flowing between the electric charge collecting electrode 9 and the electron emission element 4.

In addition, the electric charge collecting electrode 9 is disposed at the bottom of the well 12, and the cells 3 are positioned between the electric charge collecting electrode 9 and the electron emission element 4. Thereby, anions generated on the surface of the culture medium 2 by ion irradiation from the cell stimulation device 30 flow toward the bottom of the well 12, so that the cells 3 being cultured in the culture medium 2 can be electrically stimulated with high efficiency.

Other configurations are the same as in the first to third embodiments. Also, the description about the first to third embodiments applies to the fourth embodiment unless no inconsistency occurs.

Fifth Embodiment

Figure 7:
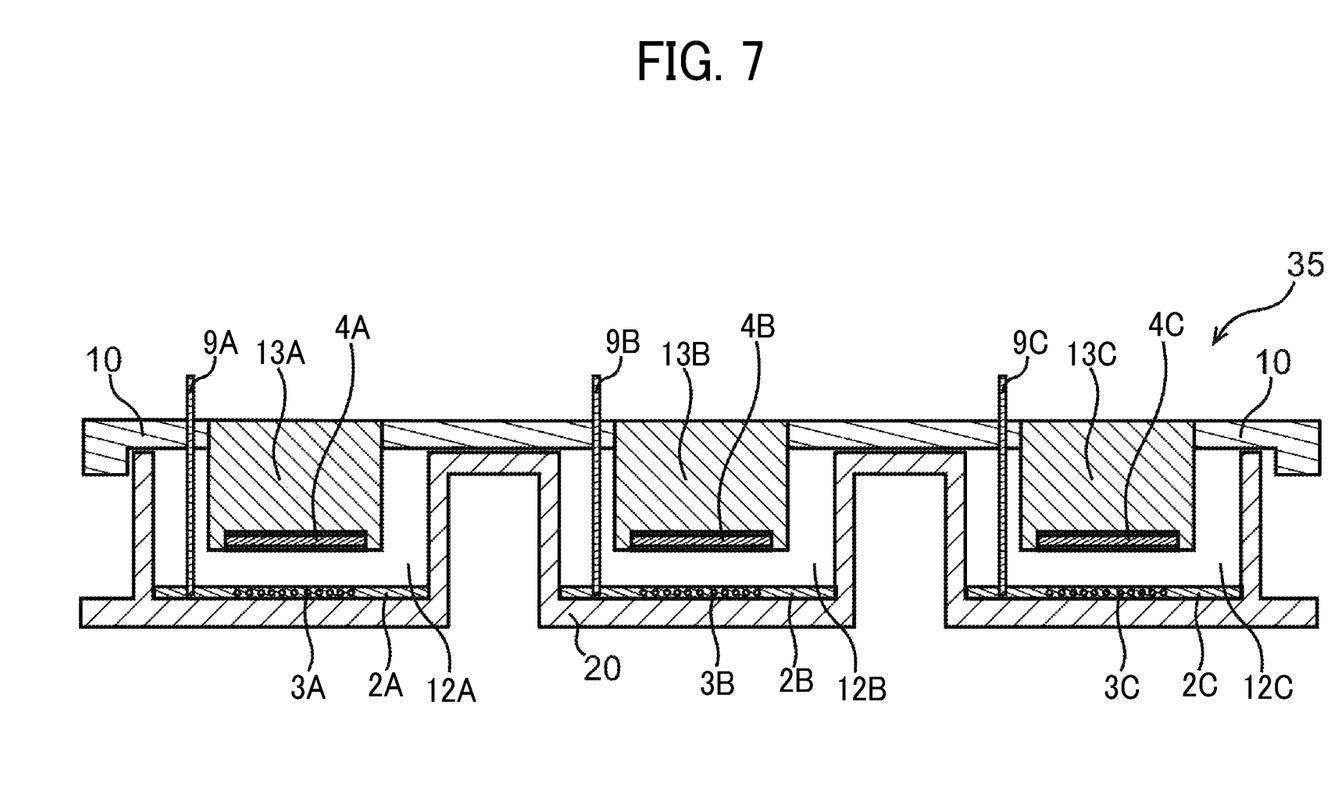
FIG. 7 is a schematic sectional view of the cell culture device according to an embodiment of the present invention.

FIG. 7 is a schematic sectional view of the cell culture device 35 according to the fifth embodiment.

In the fifth embodiment, the culture container 20 includes a plurality of wells 12a to 12c. In addition, the cell stimulation device 30 includes insulating members 13a to 13c, electron emission elements 4a to 4c, and electric charge collecting electrodes 9a to 9c, which correspond to the respective wells 12a to 12c. Such a configuration makes it possible to electrically stimulate the respective cells being cultured in the respective wells 12a to 12c in the culture container 20.

In addition, control of the voltage applied by the power supply 11 using a switching circuit makes it possible to electrically stimulate the cells only at target positions in the plurality of wells 12, at a desired timing, for a desired period.

The number of the wells 12 included in the culture container 20 is not particularly limited. For example, the culture container 20 is a 6-well plate.

In the cell stimulation device 30, the insulating member 13, the electron emission element 4, and the electric charge collecting electrode 9 may correspond to all of the wells 12 in the culture container 20, or may correspond to some of the wells 12 in the culture vessel 20.

In addition, the cell stimulation device 30 can have a structure in which a plurality of insulating members 13 are fixed to one cover member 10.

Other configurations are the same as in the first to fourth embodiments. Also, the description about the first to fourth embodiments applies to the fifth embodiment unless no inconsistency occurs.

DESCRIPTION OF REFERENCE NUMERALS 2, 2a to 2c: Culture medium
3, 3a to 3c: Cell
4, 4a to 4c: Electron emission element
5: Insulating layer
6, 6a to 6j: Lower electrode
7: Intermediate layer
8, 8a to 8j: Surface electrode
9, 9a to 9c: Electric charge collecting electrode
10: Cover member
11, 11a, 11b: Power supply
12, 12a to 12c: Well
13, 13a to 13c: Insulating member
15, 15a, 15b: First terminal
16: Second terminal
18: Incubator
20: Culture container
21: Gas phase
25, 25a, 25b: Electron emission region
30: Cell stimulation device
35: Cell culture device

The invention claimed is:

1. A cell stimulation device for stimulating cells being cultured in a culture medium, the cell stimulation device comprising:
    an electron emission element that feeds electric charges to the culture medium via a gas phase;
    an electric charge collecting electrode that collects the electric charges from the culture medium;
    an insulating member; and
    a needle-like terminal fixed to the insulating member, wherein:
    the electron emission element comprises a lower electrode, a surface electrode, and an intermediate layer disposed between the lower electrode and the surface electrode;
    the electric charge collecting electrode is disposed such that the electric charge collecting electrode is contactable with the culture medium;
    the electron emission element is fixed to the insulating member; and
    a tip of the needle-like terminal is in contact with the lower electrode.

2. The cell stimulation device according to claim 1, further comprising a power supply, wherein
    the power supply is disposed such that a voltage is applied between the lower electrode and the surface electrode, and a potential difference is generated between the electron emission element and the electric charge collecting electrode.

3. The cell stimulation device according to claim 2, wherein the power supply is electrically connected to the electron emission element and the electric charge collecting electrode such that a current generated in the gas phase by feeding the electric charges from the electron emission element to the culture medium, and a current generated in the culture medium by collecting the electric charges from the culture medium by the electric charge collecting electrode form a loop current.

4. The cell stimulation device according to claim 2, wherein the electric charge collecting electrode is grounded.

5. The cell stimulation device according to claim 1, wherein the insulating member has a slit structure on a surface thereof.

6. The cell stimulation device according to claim 1, wherein the electric charge collecting electrode is fixed to the insulating member.

7. A cell culture device comprising the cell stimulation device according to claim 1, wherein:
the culture medium is contained in a culture container; and
the insulating member is disposed on the culture container such that the surface electrode is opposite to a surface of the culture medium with the gas phase interposed between the surface electrode and the surface of the culture medium.

8. The cell culture device according to claim 7, wherein a distance between the surface electrode and the surface of the culture medium is 0.5 to 3 mm.

9. The cell culture device according to claim 7, wherein the electric charge collecting electrode is fixed to the culture container.

10. A cell stimulation device for stimulating cells being cultured in a culture medium, the cell stimulation device comprising:
an electron emission element that feeds electric charges to the culture medium via a gas phase; and
an electric charge collecting electrode that collects the electric charges from the culture medium, wherein:
the electron emission element comprises a lower electrode, a surface electrode, and an intermediate layer disposed between the lower electrode and the surface electrode;
the electric charge collecting electrode is disposed such that the electric charge collecting electrode is contactable with the culture medium;
each of the lower electrode and the surface electrode has a plurality of elongated electrodes; and
the lower electrodes and the surface electrodes are arranged in a lattice shape such that either the lower electrodes or the surface electrodes are arranged in rows, and the other of the lower electrodes or the surface electrodes are arranged in columns.

* * * * *